(12) United States Patent
Fahl

(10) Patent No.: US 10,300,233 B2
(45) Date of Patent: May 28, 2019

(54) TRACHEOSTOMA PLASTER

(71) Applicant: Andreas Fahl Medizintechnik-Vertrieb GmbH, Cologne (DE)

(72) Inventor: Andreas Fahl, Köln (DE)

(73) Assignee: Andreas Fahl Medizintechnik-Vertrieb GmbH, Cologne (DE)

( * ) Notice: Subject to any disclaimer, the term of this patent is extended or adjusted under 35 U.S.C. 154(b) by 837 days.

(21) Appl. No.: 14/818,492

(22) Filed: Aug. 5, 2015

(65) Prior Publication Data
US 2015/0335841 A1 Nov. 26, 2015

Related U.S. Application Data

(63) Continuation of application No. PCT/EP2014/000301, filed on Feb. 5, 2014.

(30) Foreign Application Priority Data

Feb. 5, 2013 (DE) .......................... 10 2013 001 910

(51) Int. Cl.
*A61M 16/04* (2006.01)
*A61F 13/02* (2006.01)
(Continued)

(52) U.S. Cl.
CPC ......... *A61M 16/047* (2013.01); *A61F 13/023* (2013.01); *A61F 13/0246* (2013.01);
(Continued)

(58) Field of Classification Search
CPC .............. A61M 16/04; A61M 16/0465; A61M 16/0468; A61M 16/047; A61M 16/0472;
(Continued)

(56) References Cited

U.S. PATENT DOCUMENTS

2003/0088219 A1   5/2003  Metz et al.
2011/0247629 A1* 10/2011  Persson ............... A61M 16/047
                                              128/207.14
(Continued)

FOREIGN PATENT DOCUMENTS

DE       69500468 T2      2/1998
DE    202006005101 U1 *   6/2006  .......... A61M 16/047
(Continued)

OTHER PUBLICATIONS

Machine translation of DE 202006005101 U1.*
(Continued)

*Primary Examiner* — Joseph D. Boecker
(74) *Attorney, Agent, or Firm* — Dinsmore & Shohl LLP

(57) ABSTRACT

To solve the problem of providing a tracheostoma plaster that has a good sealing effect in the area of skin directly bordering a tracheostoma, a tracheostoma plaster (10) is proposed, having a proximal and a distal side (12, 14), having an adhesive strip (16) arranged on the distal side, having a receptacle (36) for a tracheostoma aid and having an annular bead (20), which is arranged on the proximal side of the plaster on a portion of the same, wherein the receptacle is surrounded by the annular bead.

12 Claims, 2 Drawing Sheets

(51) Int. Cl.
*A61M 16/10* (2006.01)
*A61M 16/20* (2006.01)

(52) U.S. Cl.
CPC ....... *A61M 16/0468* (2013.01); *A61M 16/105* (2013.01); *A61M 16/1045* (2013.01); *A61M 16/20* (2013.01); *A61M 2205/0216* (2013.01)

(58) Field of Classification Search
CPC ... A61M 2210/1032; A61M 2025/0213; A61F 13/023; A61F 13/0236; A61F 13/0246
See application file for complete search history.

(56) References Cited

U.S. PATENT DOCUMENTS

| | | | |
|---|---|---|---|
| 2012/0090621 A1* | 4/2012 | van der Houwen | ........................ A61M 16/0468 128/207.16 |
| 2012/0101458 A1 | 4/2012 | Hall et al. | |
| 2013/0213404 A1* | 8/2013 | Leibitzki | ............. A61M 16/047 128/207.14 |

FOREIGN PATENT DOCUMENTS

| | | | | |
|---|---|---|---|---|
| DE | 60312327 | T2 | 11/2007 | |
| DE | 202008017105 | U1 * | 3/2009 | ........ A61M 16/0465 |
| EP | 2497449 | A2 | 9/2012 | |

OTHER PUBLICATIONS

Machine translation of DE 202008017105 U1.*
International Search Report dated Jun. 26, 2014, International Application No. PCT/EP2014/000301, filed Feb. 5, 2014.

* cited by examiner

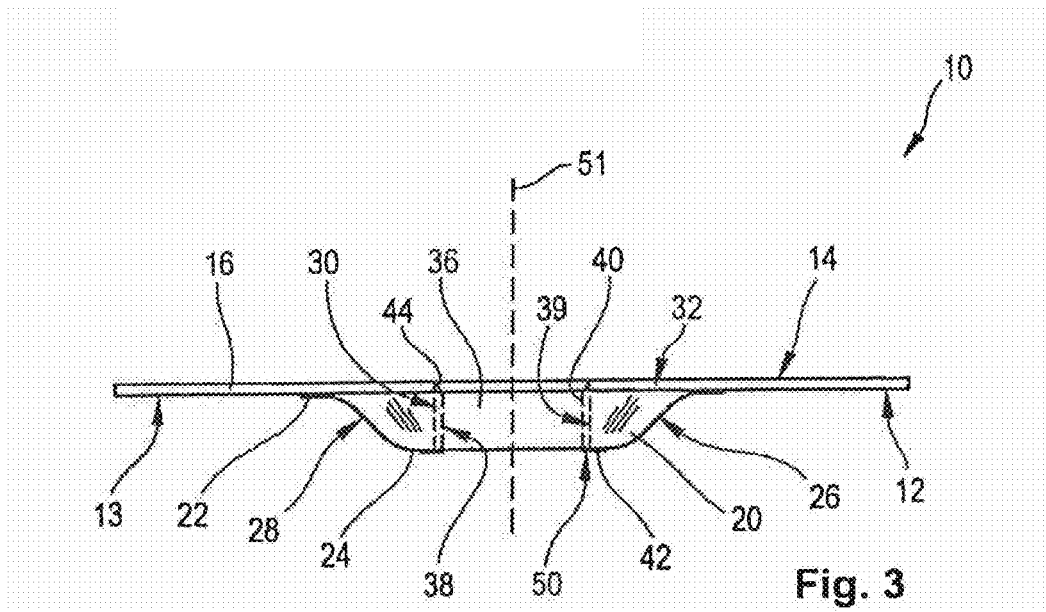
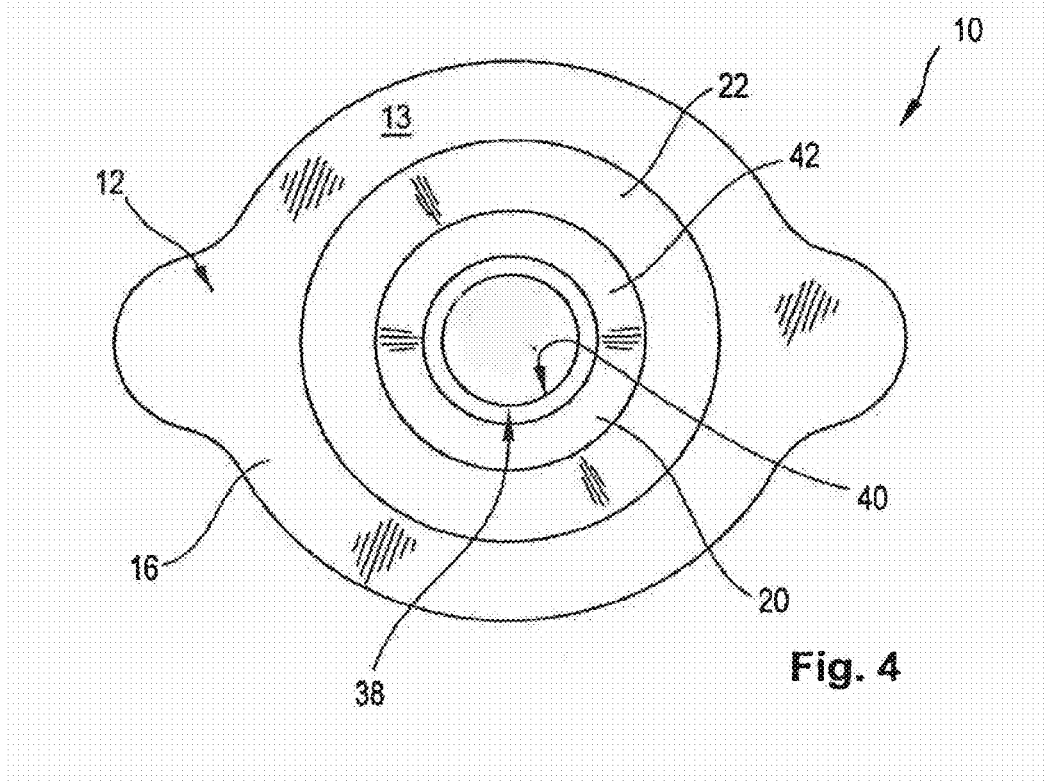

TRACHEOSTOMA PLASTER

CROSS-REFERENCE TO RELATED APPLICATIONS

This application is a continuation of PCT Patent Application PCT/EP2014/000301 filed on Feb. 5, 2014, which claims priority of German Patent Application DE 10 2013 001 910.9 filed on Feb. 5, 2013.

FIELD OF THE INVENTION

The present invention relates to a tracheostoma plaster, having a proximal and a distal side, as well as an adhesive strip.

BACKGROUND OF THE INVENTION

Tracheostoma plasters of the type mentioned above are used for attaching tracheostoma aids, such as humid moisture exchangers (HME) or speaking valves, which also have an HME function, at the Tracheostoma of a patient. A tracheostoma is an artificial opening, which may have to be created at the upper respiratory tract during a surgical procedure, so that air can be inhaled directly into the lungs, avoiding the oral cavity and larynge. For patients having a tracheostoma, it is customary to use filter systems, which serve the purpose of reproducing the regulatory mechanism for heating and humidifying the air of the patient and avoiding that the trachea is brought in contact with dry, cold and unfiltered air. As a result, irritation and an increased formation of mucus are being avoided, as well as the danger that the trachea is being clogged. By means of such filter systems, which are also called artificial noses, the inhaled air is moisturized, heated and filtered. Regularly wearing the artificial nose helps especially when there is an excessive discharge of secretion, because moistening the mucus membranes in the trachea results in reducing the secretion production.

The above-mentioned filter systems can also be provided with a speech function, such as the one disclosed in EP 1 747 792 A1. The humid moisture exchanger with speech function disclosed there has a filter box and a filter body, which is at least partially arranged in the filter box, wherein the filter box has a speaking valve arranged on its distal side, and in the interior of the filter box at least a retainer is provided for retaining the filter body. For example, the humid moisture exchanger with speech function disclosed there can be inserted in a tracheostoma plaster known from prior art, which is attached with an adhesive at the throat of the patient in such a way that the humid moisture exchanger with speech function is arranged above the tracheostoma.

A variety of such tracheo stoma plasters are also known from prior art. For example, DE 603 12 327 T2 discloses a generic tracheostoma plaster, wherein the plaster comprises a base, which is open on both ends, in order to attach a tracheostoma valve or the like to the plaster, a circular flange, which is directly connected with a proximal end of the base to the inner circumference of the flange, which concentrically surrounds this end, wherein the flange is angled or cambered toward the wall of the base, a ring-shaped tape, which is attached to the proximal side of the flange and covering the proximal side, as well as an adhesive on a proximal side of the tape. At the same time, the ring-shaped tape is designed in the form of a single-coated adhesive strip, which is attached by means of a first connection point to the inner or outer circumference of the flange and extends radially beyond the edge of the flange, wherein the ring-shaped tape is also attached by means of a second ring-shaped connection point, which is arranged between the outer circumference and the inner circumference of the flange at a radial distance from the first connection point, wherein the adhesive on the tape is covered by a protective top layer.

The tracheostoma plaster disclosed in DE 603 12 327 T2 has the disadvantage that it is relatively complicated to produce. During production, it is necessary to provide a flange, which preferably consists of polyethylene material, with an adhesive strip specifically at the first and second ring-shaped connection points, which requires a large amount of equipment. However, the tracheostoma plaster disclosed in DE 603 12 327 T2 has the advantage of providing a sufficiently safe cover, especially when the tracheostoma is deeply sucked into the throat of the patient, so that when inhaling and exhaling air is primarily guided through the tracheostoma aid inserted into the tracheostoma plaster, such as the speaking valve or the humid moisture exchanger. The tracheostoma plaster disclosed in DE 603 12 327 T2 does have the disadvantage that the flange, which consists of a relatively soft polymer, namely poly ethylene, holds a certain amount of moisture, which allows the plaster to be applied and sealed only to a certain extent to the irregular skin surfaces of the patient around the tracheostoma.

SUMMARY OF THE INVENTION

Therefore, it is the objective of the present invention to provide a tracheostoma plaster which improves the adhesion, especially when the tracheostoma is retracted, and which is also easier to produce.

According to the invention, this objective is achieved by means of a tracheostoma plaster of the type mentioned at the outset, which has an adhesive strip arranged on its distal side, a receptacle for a tracheo stoma aid, especially a speaking valve with a humid moisture exchanger or an artificial nose, as well as an annular bead arranged on the proximal side of the plaster on a portion of the same, wherein the receptacle is surrounded by the annular bead. Advantageously, when viewed in a cross section parallel to the central axis of the plaster, a proximal surface of the bead has an inflection point. At the same time, the invention-based bead can be considered as a material accumulation arranged in ring-shaped manner around the receptacle of the tracheostoma plaster. Instead of a rigid flange of the type disclosed in DE 603 12 327 T2, it is also possible to provide the proximal surface of the bead in the form of a material accumulation in such a way that the proximal surface comes in close contact with the skin surface of the patient surrounding the tracheostoma. Moreover, because of the fact that the annular bead has been arranged on the proximal side of the plaster on a portion of the same, it is relatively easy to produce the invention-based tracheostoma plaster by connecting the annular bead with an adhesive strip, which is provided at least partially with an adhesive on its proximal side, especially in the region not covered by the annular bead. It would also be practical to provide the proximal surface of the plaster in the region not covered by the annular bead completely with an adhesive. According to the invention, a proximal surface of the plaster, which is not connected with the bead, is at least partially provided with an adhesive. Customarily, the adhesive surfaces of the proximal surface of the plaster, as well as the surface of the bead, are protected by a cover strip. In terms of the present invention, a tracheostoma plaster provided with a cover strip can be considered to be adhesive. Advantageously, the annular bead consists of solid material. At the same time, the distal side of the bead has a basically planar design. An invention-based planar design is to be considered in such a way that the distal side of the bead runs approximately parallel to a smooth surface, provided by the proximal surface of the adhesive strip. As a result, by means of a planar surface on the distal side, the bead is restricted from the adhesive strip and its proximal surface, as well as from the receptacle. Advantageously, the receptacle has a radially symmetrical design, and especially a circular opening in the tracheostoma plaster, and is positioned in the center of the tracheostoma plaster. In particular, the invention-based adhesive strip is to be considered as one comprehensive adhesive layer, which forms at least partially the proximal surface of the plaster. Preferably, the adhesive strip forms the complete proximal surface of the plaster, except for the region formed by the annular bead.

In a further preferred embodiment, the bead of the invention-based tracheostoma plasters is formed by a soft, pressure-sensitive material. In terms of the present invention, pressure-sensitive means that the material returns in flexible or thermoset manner to its original position when the bead is pressed and the pressure is released again. Furthermore, the material of the bead has the characteristic that the material of the bead is displaced to adjacent regions when permanent pressure is exerted, thus increasing the sealing effect. In addition, the soft, pressure-sensitive formation of the bead results in the fact that its proximal surface has extremely good wearing properties because a comfortable feeling can be achieved in the area of skin directly bordering the tracheostoma of the patient.

In a further preferred embodiment, the bead has an outer marginal region formed approximately parallel to the adhesive strip. Preferably, it merges without any projection or evenly into the adhesive strip. Furthermore, it is preferred that an inner marginal region of the bead facing the receptacle is also designed to run approximately parallel to the adhesive strip. According to the present invention, this means that the outer and inner marginal regions of the bead are designed in parallel to a planar adhesive strip. The fact that the outer marginal region of the bead is designed approximately parallel to the adhesive strip ensures a good connection between the outer marginal region of the bead and the adhesive strip. It also results in an increased sealing effect, because a sealing effect can be achieved also in the areas of skin directly bordering the tracheostoma. However, the fact that the inner marginal region of the bead is designed approximately parallel to the adhesive strip ensures that the tracheostoma aid is securely received in the receptacle, especially when providing a mounting adapter for the tracheo stoma aid arranged in the receptacle.

Advantageously, the proximal surface of the bead has at least portions provided with an adhesive. It is especially preferred, when the proximal surface is completely provided with an adhesive. At the same time, the adhesive properties can be made available by providing an adhesive layer on the proximal surface of the bead. However, preferably, these adhesive properties can be provided by means of the bead material. When the adhesive properties are provided through the proximal surface of the bead, the seat of the tracheostoma plaster on the tracheostoma of the patient is improved. In particular, the sealing effect of the invention-based tracheostoma plaster is further improved when the solid bead, which has inherent adhesive properties, is produced from a soft, pressure-sensitive material.

In a further embodiment of the invention-based tracheostoma plaster, a mounting adapter has been arranged in the receptacle. Advantageously, the outer wall of the mounting adapter, which faces the bead, is completely covered by the bead. The connection between bead and mounting adapter, especially the outer wall of the mounting adapter, can be established in various ways. Preferably, the connection involves adhesion. However, it can also be established by means of 1 or 2 component injection molding. The connection can also be established by means of retainers, such as bolts or the like, which are arranged at the outer wall of the mounting adapter and/or the inner wall of the bead, alone or in addition in the above-mentioned types of connection. The mounting adapter can be arranged inside the receptacle in the form of a cylinder portion. As a result, it does not come in contact with the tracheostoma or the directly bordering areas of skin of the patient. Advantageously, the mounting adapter consists of a flexible material, preferably a soft, polymeric material. Advantageously, the mounting adapter consists of a polymeric material that is produced from polymers of a group comprising poly ethylene and/or poly propylene. However, it is also possible to use different polymers.

In a further embodiment, the mounting adapter has a proximal edge, which protrudes the outer circumference of the mounting adapter and is connected with the bead. Advantageously, the connection is established by means of the proximal surface of the bead. Furthermore, the connection takes place in a circular region directly adjacent to the inner wall of the bead on the proximal surface of the bead. By means of the proximal edge, the contact surface between the mounting adapter and the bead is increased so that the mounting adapter is securely retained at the bead. In a further preferred embodiment, the proximal edge of the mounting adapter merges without any projection into the bead or its proximal surface. Preferably, a proximal end of the mounting adapter forms a flush seal with the proximal surface of the bead. With each of the preceding measures, a smooth proximal surface is provided, which is facing areas of skin of the patient bordering the tracheostoma. As a result, a good sealing effect of the invention-based tracheostoma plaster is provided and irritations in the areas of skin directly bordering the tracheostoma of the patient are avoided. In terms of the invention, the term "without any projection" is to be understood in such a way that a smooth, flush transition is made between the means under discussion without any formation of edges, grooves or the like.

In a further embodiment, a distal end of the mounting adapter forms a flush seal with a distal surface of the bead. As a result, the invention-based tracheostoma plaster has no elevation on its distal side but provides an even appearance, which is preferred by the patient.

BRIEF DESCRIPTION OF THE DRAWINGS

By means of the following examples, these and other advantages are explained in more detail. It is shown:

FIG. 3 a side view of the tracheostoma plaster according to FIG. 1; and

FIG. 4 a bottom view of the tracheostoma plaster according to FIG. 1.

DETAILED DESCRIPTION OF THE PREFERRED EMBODIMENTS

Figure 1:
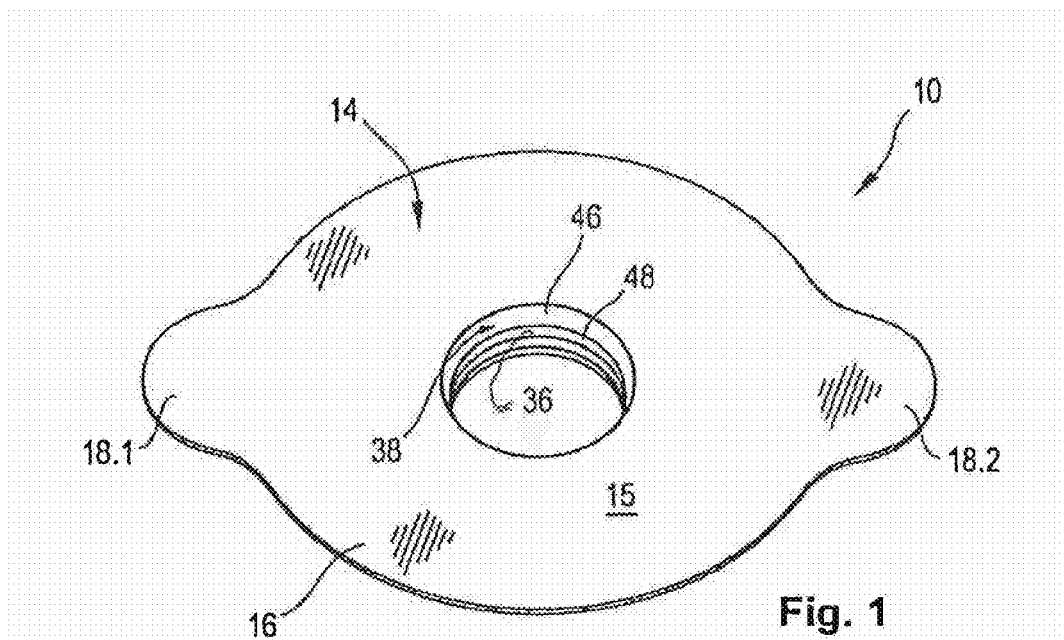
FIG. 1 a perspective top view of an invention-based tracheostoma plaster.

First of all, it should be mentioned that the embodiment of the invention-based tracheostoma plaster shown in the figures is nonrestrictive. Instead, the characteristics described there can be combined with the characteristics described above to form different embodiments. Furthermore, it should be mentioned that the reference numerals mentioned in the description of the figures do not restrict the scope of protection of the present invention but should make reference merely to the embodiments shown in the figures. Subsequently, similar parts or parts with similar functions have the same reference numerals. It should be especially emphasized that the exemplary design shown in the figures, which have a basically circular form and two lateral lugs demonstrate merely one of the possible embodiments of the invention-based tracheostoma plaster. For example, the basic form could also be oval, rectangular, or have four, five, six or more corners. At the same time, the embodiment could include lugs or it could come without lugs. Provision could also be made for provisional lugs (not shown in the embodiments), which have the purpose of facilitating the removal of the plaster from a cover patch (not shown) protecting the adhesive strip. It should also be mentioned that the receptacle 36 does not always have to be arranged in a concentric and central manner, as shown in the embodiments of the present invention. Instead, the receptacle can also be displaced toward the head of the patient or in reverse direction. As shown in FIG. 3, when viewed in cross-section, the proximal surface of the bead can also be arranged in any other form and does not have to comprise an inflection point. In addition, the mounting adapter 38 does not have to include a proximal edge 42. In this case, a proximal end 50 of the mounting adapter can form a flush seal with a proximal surface of the bead 20.

FIG. 1 shows an invention-based tracheostoma plaster 10 or body having a distal side 14 facing away from the user and a proximal side 12 facing the user. The plaster 10 includes an adhesive strip 16. The adhesive strip 16 forms a completely adhesive surface 13 of the plaster 10 in its proximal side 12 in the region surrounding the bead 20. The adhesive strip of the plaster is provided with a distal surface 15, which is non-adhesive. The plaster has a basically circular form, wherein opposite lugs 18.1 and 18.2 have been arranged on two sides, which in particular serve the purpose of facilitating the removal of the plaster 10 from the skin of the patient.

The plaster has a receptacle 36, which has been arranged in a concentric and central manner in the plaster 10, and in which a mounting adapter 38 with an inner wall 40 has been arranged. About half way up of the bead 20 (not shown in FIG. 1), the mounting adapter 38 has a bulge 48 at least on the inner wall 40. This results in a secure seat of a tracheostoma aid, such as an artificial nose or a speaking valve, which is to be inserted in the receptacle 36. The insertion of such a tracheostoma aid is further facilitated by providing a chamfered edge 46 in the end region of the mounting adapter 38 facing the distal side 14 of the plaster 10.

Figure 2:
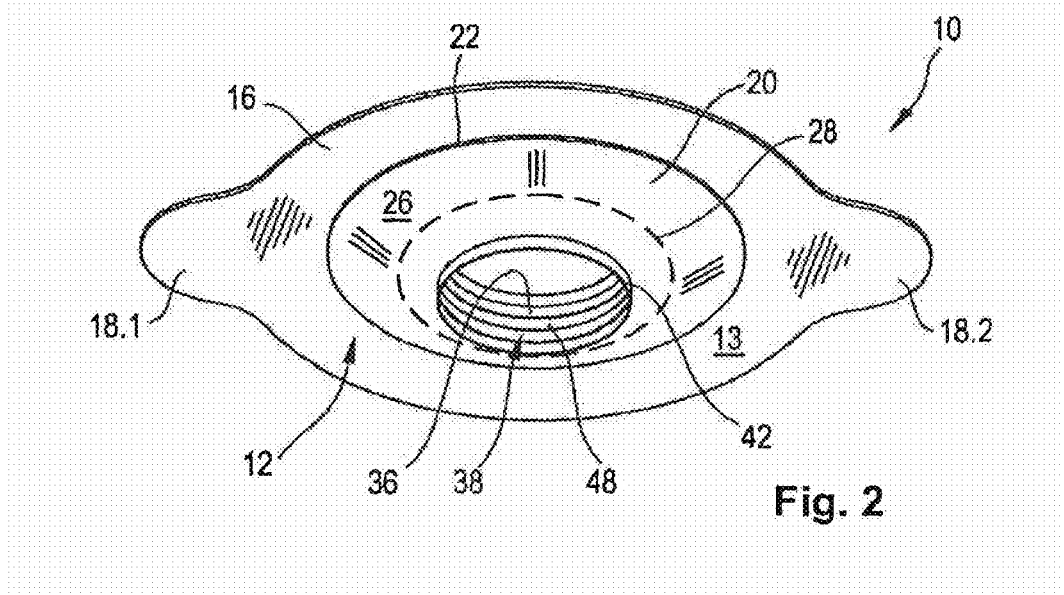
FIG. 2 a perspective bottom view of an invention-based tracheostoma plaster.

FIG. 2 shows the plaster 10 according to FIG. 1 in a perspective view from the bottom. On the proximal side 12 of the plaster 10, an annular bead 20 has been arranged, which is designed in circumferential manner around the receptacle 36. At the same time, the bead 20 has an outer marginal area 22, which runs basically parallel to the adhesive strip 16 (FIG. 3). Furthermore, FIG. 2 shows an inflection point 28 of the bead 20 indicated with a dotted line.

FIG. 2 also shows an embodiment of the mounting adapter 38 in that the mounting adapter 38 has a proximal edge 42, which is connected with a proximal surface 26 of the bead 20 in a circular area around the receptacle 36. In an alternative embodiment, this edge 42 can also be omitted. In this case, the proximal end 50 of the mounting adapter 38 (see FIG. 3) preferably merges without any projection or flush into the bead 20.

FIG. 3 shows an excellent view of the tracheostoma plaster according to FIG. 1 and FIG. 2, especially with regard to the design of the bead 20. The proximal surface 26 of the bead 20 comprises the inflection point 28. In terms of the present invention, the term inflection point is to be understood in a mathematical sense. The inflection point 28 is located in the center between the outer marginal area 22 and the inner marginal area 24 of the bead 20, each of which is situated approximately parallel to the adhesive strip 16. The bead 20 has an inner wall 30 on which the mounting adapter 38 is directly located. The mounting adapter 38 has an outer wall 39, which is completely covered by the bead 20. The mounting adapter 38 has the proximal edge 42 which surrounds the bead 20 and which is directly adjacent and connected to the bead 20. At the same time, the proximal edge 42 merges without any projection into the material of the bead 20 or its surface 26.

The inflection point 28 is defined by a cross-section through the plaster 10, namely a cross-section through the plaster parallel to a centerline of the plaster.

The mounting adapter 38 has an inner, cylindrical wall 40, which has a distal end 44 and the proximal end 50. At the same time, the distal end 44 of the mounting adapter 38 forms a flush seal with a distal surface 32 of the bead 20. Moreover, the distal end 44 can be covered by the adhesive strip 16.

FIG. 4 shows a bottom view of the tracheostoma plaster 10 according to FIGS. 1 to 3, which clearly shows that the bead 20 has an outer edge 22. The figure also shows the arrangement of the mounting adapter 38 in the receptacle 36 having the proximal edge 42.

At the same time, FIGS. 1 to 4 do not show a cover strip, which is arranged on the proximal side 12 of the plaster 10 at least in the region of the free bottom side of the adhesive strip 16, which, preferably, has a completely adhesive design and forms the proximal surface 13. In particular, the cover strip can cover the bead 20 also when the proximal surface 26 of the bead is at least partially adhesive. However, the proximal surface 26 of the bead 20 can also be covered merely to provide protection.

By means of the present invention, a tracheostoma plaster is provided, which, advantageously, can be applied in an easy manner and which has an excellent sealing effect in the area of skin directly bordering the tracheostoma of the patient, and which is also easy to produce.

The invention claimed is:
1. A tracheostoma plaster comprising:
a body having a proximal side and a distal side, an adhesive strip arranged on the distal side of the body, said body having a receptacle for a tracheostoma aid, the receptacle having a mounting adapter for the tracheostama aid and a distal end with a chamfered edge for guiding the tracheostoma aid into the receptacle, said body having an annular bead arranged on a portion of the proximal side, the annular bead having an inner wall and a proximal surface, wherein the receptacle is fully surrounded by the inner wall of the annular bead.

2. A tracheostoma plaster according to claim 1, wherein the bead further comprises a proximal surface having an inflection point when viewed from a cross-section that runs parallel to a centerline of the plaster.

3. A tracheostoma plaster according to claim 1, wherein the bead has an outer marginal area running approximately parallel to the adhesive strip.

4. A tracheostoma plaster according to claim 1, wherein the bead consists of a soft, pressure-sensitive material.

5. A tracheostoma plaster according to claim 1, wherein the distal side of the bead has a basically planar design.

6. A tracheostoma plaster according to claim 1, wherein an inner marginal area of the bead attached to the receptacle is generally parallel to the adhesive strip.

7. A tracheostoma plaster according to claim 1, wherein the receptacle has a proximal edge, which is connected with the bead.

8. A tracheostoma plaster according to claim 7, wherein the proximal edge merges without any projection into the bead.

9. A tracheostoma plaster according to claim 1, wherein the receptacle consists of a flexible material.

10. A tracheostoma plaster according to claim 1, wherein a distal end of the mounting adapter forms a flush seal with a distal surface of the bead.

11. A tracheostoma plaster according to claim 1, wherein the mounting adapter has a proximal end merging with the bead.

12. A tracheostoma plaster according to claim 1, wherein at least portions of the proximal surface of the plaster, which are not connected with the bead, are adhesive.

* * * * *